US010561848B2

(12) United States Patent
Xiao et al.

(10) Patent No.: US 10,561,848 B2
(45) Date of Patent: Feb. 18, 2020

(54) SYSTEMS AND METHODS FOR PROGRAMMING AND OPERATING DEEP BRAIN STIMULATION ARRAYS

(71) Applicant: REGENTS OF THE UNIVERSITY OF MINNESOTA, Minneapolis, MN (US)

(72) Inventors: YiZi Xiao, Eden Prairie, MN (US); Edgar Peña, Saint Paul, MN (US); Matthew Douglas Johnson, North Oaks, MN (US)

(73) Assignee: REGENTS OF THE UNIVERSITY OF MINNESOTA, Minneapolis, MN (US)

(*) Notice: Subject to any disclaimer, the term of this patent is extended or adjusted under 35 U.S.C. 154(b) by 223 days.

(21) Appl. No.: 15/291,628

(22) Filed: Oct. 12, 2016

(65) Prior Publication Data
US 2017/0100601 A1    Apr. 13, 2017

Related U.S. Application Data

(60) Provisional application No. 62/240,644, filed on Oct. 13, 2015.

(51) Int. Cl.
*A61N 1/372*     (2006.01)
*A61N 1/05*      (2006.01)
*A61N 1/36*      (2006.01)

(52) U.S. Cl.
CPC ....... *A61N 1/37247* (2013.01); *A61N 1/0534* (2013.01); *A61N 1/36146* (2013.01)

(58) Field of Classification Search
CPC ............. A61N 1/37247; A61N 1/0534; A61N 1/36146; A61N 1/36067; A61N 1/36082
See application file for complete search history.

(56) References Cited

U.S. PATENT DOCUMENTS

| 4,432,360 A | 2/1984 | Mumford |
| 5,443,486 A | 8/1995 | Hrdlicka |
| 5,713,922 A | 2/1998 | King |
| 5,814,092 A | 9/1998 | King |

(Continued)

FOREIGN PATENT DOCUMENTS

| EP | 2321002 | 4/2014 |
| WO | WO 2004/096349 | 11/2004 |

(Continued)

OTHER PUBLICATIONS

Application and File History for U.S. Appl. No. 15/794,333, filed Oct. 26, 2017, Inventors: Johnson et al.

(Continued)

*Primary Examiner* — Paula J Stice
(74) *Attorney, Agent, or Firm* — Patterson Thuente Pedersen, P.A.

(57) ABSTRACT

Systems, methods and apparatus for determining and/or programming stimulation settings for a pulse generator capable of steering current to a deep brain stimulation array are disclosed. Individual patient brain geometry and lead specific geometry data can be used to generate a maximum activation function curve. Optimization methods can be used to find stimulation settings that are as close as possible to achieving the value of the maximum activation function curve.

10 Claims, 7 Drawing Sheets

(56) References Cited

U.S. PATENT DOCUMENTS

| | | | |
|---|---|---|---|
| 6,463,328 B1 | 10/2002 | John |
| 6,587,724 B2 | 7/2003 | Mann |
| 6,622,048 B1 | 9/2003 | Mann |
| 7,003,349 B1 | 2/2006 | Anderson |
| 7,035,690 B2 | 4/2006 | Goetz |
| 7,110,821 B1 | 9/2006 | Ross |
| 7,146,223 B1 | 12/2006 | King |
| 7,177,674 B2 | 2/2007 | Echauz |
| 7,181,286 B2 | 2/2007 | Sieracki |
| 7,184,837 B2 | 2/2007 | Goetz |
| 7,187,978 B2 | 3/2007 | Christopherson |
| 7,209,787 B2 | 4/2007 | DiLorenzo |
| 7,239,926 B2 | 7/2007 | Goetz |
| 7,254,445 B2 | 8/2007 | Law |
| 7,266,412 B2 | 9/2007 | Stypulkowski |
| 7,305,268 B2 | 12/2007 | Gilner |
| 7,346,382 B2 | 3/2008 | McIntyre |
| 7,415,308 B2 | 8/2008 | Gerber |
| 7,463,927 B1 | 12/2008 | Chaouat |
| 7,463,928 B2 | 12/2008 | Lee |
| 7,489,970 B2 | 2/2009 | Lee |
| 7,519,431 B2 | 4/2009 | Goetz |
| 7,548,786 B2 | 6/2009 | Lee |
| 7,551,960 B2 | 6/2009 | Forsberg |
| 7,657,319 B2 | 2/2010 | Goetz |
| 7,676,273 B2 | 3/2010 | Goetz |
| 7,680,526 B2 | 3/2010 | McIntyre |
| 7,720,548 B2 | 5/2010 | King |
| 7,801,618 B2 | 9/2010 | Pless |
| 7,826,902 B2 | 11/2010 | Stone |
| 7,860,548 B2 | 12/2010 | McIntyre |
| 7,904,134 B2 | 3/2011 | McIntyre |
| 7,957,809 B2 | 6/2011 | Bourget |
| 8,090,446 B2 | 1/2012 | Fowler |
| 8,121,694 B2 | 2/2012 | Molnar |
| 8,180,451 B2 | 5/2012 | Hickman |
| 8,180,601 B2 | 5/2012 | Butson |
| 8,290,596 B2 | 10/2012 | Wei |
| 8,326,433 B2 | 12/2012 | Blum |
| 8,379,952 B2 | 2/2013 | McIntyre |
| 8,483,836 B2 | 7/2013 | Polefko |
| 8,538,543 B2 * | 9/2013 | McIntyre | A61N 1/0534 600/407 |
| 8,620,452 B2 | 12/2013 | King |
| 8,644,946 B2 | 2/2014 | Butson |
| 8,649,845 B2 | 2/2014 | McIntyre |
| 8,649,872 B2 | 2/2014 | Lee |
| 8,666,506 B2 | 3/2014 | Goetz |
| 8,694,127 B2 | 4/2014 | Pianca |
| 8,712,539 B2 | 4/2014 | Goetz |
| 8,725,269 B2 | 5/2014 | Nolan |
| 8,757,485 B2 | 6/2014 | Drees |
| 8,781,592 B2 | 7/2014 | Polefko |
| 8,805,518 B2 | 8/2014 | King |
| 8,812,126 B2 | 8/2014 | Butson |
| 8,838,242 B2 | 9/2014 | Goetz |
| 8,914,121 B2 | 12/2014 | Moffitt |
| 9,067,076 B2 | 6/2015 | Bauhahn |
| 9,101,276 B2 | 8/2015 | Georgopoulos |
| 2004/0199216 A1 | 10/2004 | Lee |
| 2004/0267330 A1 | 12/2004 | Lee |
| 2005/0060001 A1 | 3/2005 | Singhal |
| 2005/0203588 A1 | 9/2005 | King |
| 2006/0217781 A1 | 9/2006 | John |
| 2006/0235472 A1 | 10/2006 | Goetz |
| 2007/0043268 A1 | 2/2007 | Russell |
| 2007/0203545 A1 | 2/2007 | Cooke |
| 2007/0083104 A1 | 4/2007 | Butson |
| 2007/0185544 A1 | 8/2007 | Dawant |
| 2007/0203538 A1 | 8/2007 | Stone |
| 2007/0244519 A1 | 10/2007 | Keacher |
| 2008/0027514 A1 | 1/2008 | DeMulling |
| 2008/0103552 A1 | 5/2008 | Goetz |
| 2008/0208284 A1 | 8/2008 | Rezai |
| 2008/0215118 A1 | 9/2008 | Goetz |
| 2009/0082829 A1 | 3/2009 | Panken |
| 2009/0105787 A1 | 4/2009 | Kokones |
| 2009/0112281 A1 | 4/2009 | Miyazawa |
| 2009/0118787 A1 | 5/2009 | Moffitt |
| 2010/0228314 A1 | 9/2010 | Goetz |
| 2011/0040351 A1 | 2/2011 | Butson |
| 2011/0066407 A1 | 3/2011 | Butson |
| 2011/0160796 A1 | 6/2011 | Lane |
| 2011/0172737 A1 | 7/2011 | Davis |
| 2011/0191275 A1 | 8/2011 | Lujan |
| 2011/0264165 A1 | 10/2011 | Molnar |
| 2011/0313268 A1 | 12/2011 | Kokones |
| 2012/0016378 A1 | 1/2012 | Pianca |
| 2012/0277828 A1 | 11/2012 | O'Connor |
| 2013/0226261 A1 | 8/2013 | Sparks |
| 2014/0350634 A1 | 11/2014 | Grill |

FOREIGN PATENT DOCUMENTS

| | | |
|---|---|---|
| WO | WO 2005/028022 | 3/2005 |
| WO | WO 2007/102945 | 9/2007 |
| WO | WO2008/005513 | 1/2008 |
| WO | WO 2008/070145 | 9/2008 |
| WO | WO 2009/055207 | 4/2009 |
| WO | WO 2009/134475 | 11/2009 |
| WO | WO 2010/065888 | 6/2010 |
| WO | WO2011/094752 | 8/2011 |
| WO | WO 2013/162681 | 10/2013 |

OTHER PUBLICATIONS

Barbas et al., *Toward Patient-Specific Targeting and Parameter Setting of Deep Brain Stimulation for Relief of Depression*, Biol Phychiatry © 2014, pp. 914-196, available at http://dx.doi.org/10.1016/j.biopsych.2014.09.012.

Barbe et al., *Individualized Current-Shaping Reduces DBS-Induced Dysarthria in Patients with Essential Tremor*, © 2014, American Academy of Neurology, 7 pages.

Berenstein, *Current Steering and Current Focusing in Cochlear Implants: Comparison of Monopolar, Tripolar and Virtual Channel Electrode Configurations*, © 2008, pp. 250-260.

Buhlmann, *Modeling of a Segmented Electrode for Desychnronizing Deep Brain Stimulation*, Dec. 2011, vol. 4, Article 15, pp. 1-8.

Butson, Christopher, *Patient-Specific Analysis of the Volume of Tissue Activated During Deep Brain Stimulation*, NIH Public Access, Jan. 15, 2007, pp. 1-16.

Butson, Christopher, *Patient-Specific Analysis of the Volume of Tissue Activated During Deep Brain Stimulation*, NIH Public Access, Jan. 2008, pp. 1-16.

Butson, C.R., *StimExplorer: Deep Brain Stimulation Parameter Selection Software System*, © Springer-Verlag 2007, 97(2), pp. 569-574.

Butson, Christopher R., IEEE Trans Vis Comput Graph, *Evaluation of Interactive Visualization on Mobile Computing Platforms for Selection of Deep Brain Stimulation Parameters*, Jan. 2013, 19(1), pp. 108-117.

Chatuvedi, Ashutosh et al., *Patient-Specific Models of Deep Brain Stimulation: Influence of Field Model Complexity on Neural Activation Predictions*, Apr. 1, 2010, 3(2), 23 pages.

Chatuvedi, Ashutosh et al., *Current Steering to Activate Targeted Neural Pathways During Deep Brain Stimulation of the Subthalamic Region*, Jul. 2012, 5(3), 16 pages.

Chatuvedi, Ashutosh et al., *Artificial Neural Network Based Characterization of the Volume of Tissue Activated During Deep Brain Stimulation*, NIH Public Access, J. Neural Eng., Oct. 2013, 17 pages.

Choi, Charles T. M., IEEE, *Modeling Deep Brain Stimulation Based on Current Steering Scheme*, vol. 47, No. 5, May 2011, pp. 890-893.

Cicione, Rosemary, Visual Cortex Response to Paired Stimulation of Retina, *Spatiotemporal Interactions in the Visual Cortex Following Paired Electrical Stimulation of the Retina*, © 2014, vol. 55, No. 12, pp. 7726-7738.

(56) References Cited

OTHER PUBLICATIONS

Contarino, M. Fiorella et al., Research Gate, *Directional Steering—A Novel Approach to Deep Brain Stimulation*, Sep. 2014 and as retrieved on Oct. 2, 2018, 9 pages.
Dumm, Gerald, *Virtual Electrodes by Current Steering in Retinal Prostheses*, vol. 55, No. 12, Dec. 2014, available at https://iovs.arvojournals.org/pdfaccess.ashx?url=/data/journals/iovs/933678/, as retrieved on Oct. 3, 2018, pp. 8078-8085.
Firszt, Jill B et al., *Current Steering Creates Additional Pitch Percepts in Adult Cochlear Implant Recipients*, © 2007, Otology & Neurotolgy, Inc. , pp. 629-636.
Frankemolle, Anneke M.M., Brain: A Journal of Neurology, Brain 2010: 133, *Reversing Cognitive-Motor Impairments in Parkinson's Disease Patients Using a Computational Modelling Approach to Deep Brain Stimulation Programming*, pp. 746-761.
Oxford University, Brain: A Journal of Neurology, *Steering Technology for Deep Brain Stimulation*, © 2014, pp. 1854-1862.
Horsager, Alan et al., Visual Psychophysics and Physiological Optics, *Spatiotemporal Interactions in Retinal Prosthesis Subjects*, Feb. 2010, Vo. 51, No. 2, pp. 1223-1233.
Hunka, Karen, Journal of Neuroscience Nursing, *Nursing Time to Program and Assess Deep Brain Stimulators in Movement Disorder Patients*, Aug. 2005, vol. 37, No. 4, pp. 204-210.
Jepson, Lauren H. et al., Neurobiology of Disease, *Spatially Patterned Electrical Stimulation to Enhance Resolution of Retinal Prostheses*, Apr. 2, 2014, 34(14), pp. 4871-4881.
Keane, Maureen, NIH Public Access, J. Neural Eng. , *Improved Spatial Targeting with Directionally Segmented Deep Brain Stimulation Leads for Treating Essential Tremor*, Aug. 2012, 9(4), 18 pages.
Kumar, Rajeev, *Methods for Programming and Patient Management with Deep Brain Stimulation of the Globus Pallidus for the Treatment of Advanced Parkinson's Disease and Dystonia*, Movement Disorders, Mar. 28, 2002, 2 pages.
Kuncel, Alex M., Clin Ceurophysiol, Sep. 2008, *A Method to Estimate the Spatial Extent of Activation in Thalamic Deep Brain Stimulation*, Sep. 2008, 20 pages.
Coenen, V.A. et al., *Explaining Clinical Effects of Deep Brain Stimulation Through Simplified Target-Specific Modeling of the Volume of Activated Tissue*, AJNR 33, www.ajnr.org, 9 pages.
Martens H.C.F, Clinical Neurophysiology, *Spatial Steering of Deep Brain Stimulation Volumes Using a Novel Lead Design*, © 2010, 9 pages.
McIntyre, Cameron C., Conf Proc IEEE Eng Med Biol. , *Customizing Deep Brain Stimulation to the Patient Using Computational Models*, 2009, 5 pages.
McIntyre, Cameron C., Clinical Neurophysiology, *Electric Field and Stimulating Influence Generated by Deep Brain Stimulation of the Subthatlamic Nucleus*, © 2004, 7 pages.
McIntyre, Cameron C. et al., 33$^{rd}$ Annual International Conference of the IEEE EMBS, *Improving Postural Stability via Computational Modeling Approach to Deep Brain Stimulation Programming*, Aug. 30 through Sep. 3, 2011, 2 pages.
Miocinvoic, Svjetlana, Parkinsonism and Related Disorders, Elservier, *Outcomes, Management and Potential Mechanisms of Interleaving Deep Brain Stimulation Settings*, 2014, 4 pages.
Montgomery Jr, E.B., *Deep brain stimulation programming: principles and practice*, 2010: Oxford University Press, 201 pages.
Moro, Elena, *Subthalaic Nucleus Stimulation: Improvements in Outcome with Reprogramming*, American Medical Association, © 2006, pp. 1266-1272.
Opie, N.L. et al., 35$^{th}$ Annual International Conference of the IEEE EMBS, *Current Steering for High Resolution Retinal Implants*, © 2013, Jul. 3-7, 2013, 5 pages.
Kuncel, Alexis M., *Selection of Stimulus Parameters for Deep Brain Stimulation*, Science Direct, vol. 115, Issue 11, Nov. 2004, pp. 2431-2441.
Phibbs, Fenna T. et al., *Use of Efficacy Probability Maps for the Post-Operative Programming of Deep Brain Stimulation in Essential Tremor*, Parkinsonism Relat Disord, Dec. 2014, 11 pages.
Pollo Claudio et al., Brain: A Journal of Neurology, *Directional Deep Brain Stimulation: An Intraoperative Double-Blind Pilot Study*, 2015, 12 pages.
Bonham, Ben H. et al., Hear Res. , *Current Focusing and Steering: Modeling, Physiology and Psychophysics*, Aug. 2008, 27 pages.
Schuurman, Rick et al., Stereotact Funct Neurosurg, *Papers Session—Stereotactic Technology* , May 29, 2013, 1 page.
Toader, Emil et al., 32$^{nd}$ Annual International Conference of the IEEE EMBS, *Steering Deep Brain Stimulation Fields Using a High Resolution Electrode Array*, Aug. 31 through Sep. 4, 2010, 4 pages.
Townshend Brent, *Reduction of Electrical Interaction in Auditory Prostheses*, IEEE Transactions on Biomedical Engineering, vol. BME-34, No. 11, Nov. 1987, pp. 891-897.
Veraart, Claude, *Selective Control of Muscle Activation with a Multipolar Nerve Cuff Electrode*, IEEE Transactions on Biomedical Engineering, vol. 40, No. 7, Jul. 1993, pp. 640-653.
Volkmann, Jens et al., *Introduction to the Programming of Deep Brain Stimulators*, Movement Disorders, vol. 17, Suppl. 3, 2002, pp. S181-S187.
Xiao, YiZi et al., *Theoretical Optimization of Stimulation Strategies for Directionally Segmented Deep Brain Stimulation Electrode Arrays*, Dec. 23, 2014, 31 pages.
Volkmann, Jens, *Basic Algorithms for the Programming of Deep Brain Stimulation in Parkinson's Disease*, Movement Disorders, vol. 21, Issue S514, Jun. 29, 2006.
Xiao-Jiang, Feng, *Optimal Deep Brain Stimulation of the Subthalamic Nucelus—A Computational Study*, Journal of Computational Neuroscience, Dec. 2007.

\* cited by examiner

SYSTEMS AND METHODS FOR PROGRAMMING AND OPERATING DEEP BRAIN STIMULATION ARRAYS

RELATED APPLICATION

The present application claims the benefit of U.S. Provisional Application No. 62/240,644 filed Oct. 13, 2015, which is hereby incorporated herein in its entirety by reference.

STATEMENT REGARDING FEDERALLY SPONSERED RESEARH OR DEVELOPMENT

This invention was made with government support under NS081118 awarded by the National Institutes of Health. The government has certain rights in the invention.

TECHNICAL FIELD

The present disclosure relates generally to brain stimulation, and more particularly to systems and methods for deep brain stimulation via electrode arrays.

BACKGROUND

Deep brain stimulation (DBS) is an effective surgical procedure for the treatment of a number of neurological and neuropsychiatric disorders, including medication-refractory Parkinson's disease (PD), essential tremor (ET), dystonia, and severe obsessive compulsive disorder. The procedure involves placing an electrode lead into a brain region to modulate abnormal neuronal activity with various forms of pulsatile electrical stimulation. Successful treatment can be characterized by both symptom suppression and lack of side-effects. Such success requires accurate lead placement as well as spatially targeted stimulation settings to avoid activating regions that elicit, for example, adverse motor, sensory, and/or cognitive side-effects for the patient.

Traditional designs of DBS leads (for example, the Medtronic Model 3387/3389) use four cylindrical electrodes to deliver current in an omnidirectional fashion around the lead. An improvement to this design is to enable the steering of current delivery both along and around the DBS lead, via, for example, circumferentially-segmented electrodes. Such a DBS array (DBSA) might have, for example, 32 electrodes arranged in eight rows of four electrodes each. These DBS arrays are especially useful in cases of off-target DBS implants and for small or complex-shaped brain targets, such as the subthalamic nucleus or the pedunculopontine nucleus.

With the larger number of electrodes available in a DBSA lead, programming, operation and/or control challenges have emerged. While manual testing of potential settings is feasible with traditional four electrode DBS leads, the number of possible combinations is unwieldy, and thus a need exists for efficient, effective, and safe methods of operating, controlling and/or programming DBSA settings, as conventional approaches to programming DBSAs have numerous drawbacks.

Conventional manual programming of DBSA settings works much like an optometrist performing a vision examination. A clinician will manually test many stimulation settings and evaluate the patient's response to each in order to determine the best one to use. This process can take hours within a single clinical visit and often several clinical visits over the course of weeks to months to optimize.

Conventional feedback-based systems have embedded technology to log and analyze patient response information or certain biomarkers (such as features in brain waves) in order to inform and update stimulation configurations. Sometimes a rating/ranking system is in place to determine the best configuration based on these responses/biomarkers.

Conventional brain mapping has been used by some researchers who have compiled intraoperative microelectrode stimulation data and mapped them onto a human brain atlas. An efficacy probability map is thus created by assigning every location on the brain atlas a probability for delivering therapeutic stimulation. The probability assignment is based on overlapping normal distributions with therapeutic stimulation sites at the center of each distribution. Finally, the efficacy probability map (brain atlas) is nonlinearly warped onto the patient's pre-operative MRI and used to determine the electrode settings that may deliver the best therapy. This approach is entirely based on empirical patient data.

Finally, conventional patient anatomy-based computational neuron models can be used to predict the best stimulating electrode settings for modulating a particular pathway or pathways within the brain. A therapeutic target volume in the brain is segmented and reconstructed from the patient's MRI data. The volume is populated with simulated model neurons and virtual stimulation is applied to them. The tissue enclosed by the activated neurons under virtual DBS is termed "volume of tissue activated" (VTA). Large numbers of simulations are run in order to account for the different stimulating electrode configurations, neuron orientations and locations. The solutions for each simulation are stored in a large lookup table. Given a new target volume for stimulation, the pre-compiled database can be searched for the setting that gives the most overlap between the solution VTA and the target volume.

In summary, conventional approaches for programming deep brain stimulation systems cannot scale well to DBSAs with more than a handful of electrodes. Manual and feedback-based programming methods can be tailored to the patient but can take too much time and resources to implement effectively. Mapping methods are limited by the availability of a sufficiently rich source database and do not take the unique structure of a patient's brain tissue into account. Finally, conventional computational models require vast computational resources that may not be present in a clinical setting.

SUMMARY

The present disclosure discusses model-based and objective systems and methods for operating, controlling and/or programming DBSAs that are based on individual patient data and are computationally efficient. In embodiments, methods and systems can use the superposition of electric fields to optimize electrode configurations in programming, controlling and/or operating high-density deep brain stimulation DBSAs. This is in contrast to conventional approaches that rely on biophysically complex neuron models to determine optimal electrode configurations. The optima computed from this new approach can also be tailored to user-specific battery power constraints.

In an embodiment, a method for determining a stimulation setting for each electrode in a deep brain stimulation array having one or more electrodes involves receiving brain geometry data (for example, from an MM), receiving lead geometry data (for example, from a CT scan), generating from the brain and lead geometry data one or more grid points representing a target tissue to be activated, calculating a maximum activation function value for each of the one or more grid points, and then performing a convex optimization method to determine a set of stimulation settings for each electrode such that the actual activation function value for each grid point is as close to the maximum activation function value for the grid points of interest.

In embodiments, the convex optimization method can use maximum deviation, linear programming, or quadratic programming to determine the optimal settings.

The above summary is not intended to describe each illustrated embodiment or every implementation. The figures and the detailed description that follow more particularly exemplify these embodiments.

BRIEF DESCRIPTION OF THE DRAWINGS

Embodiments may be more completely understood in consideration of the following detailed description in connection with the accompanying drawings, in which.

Figure 1:
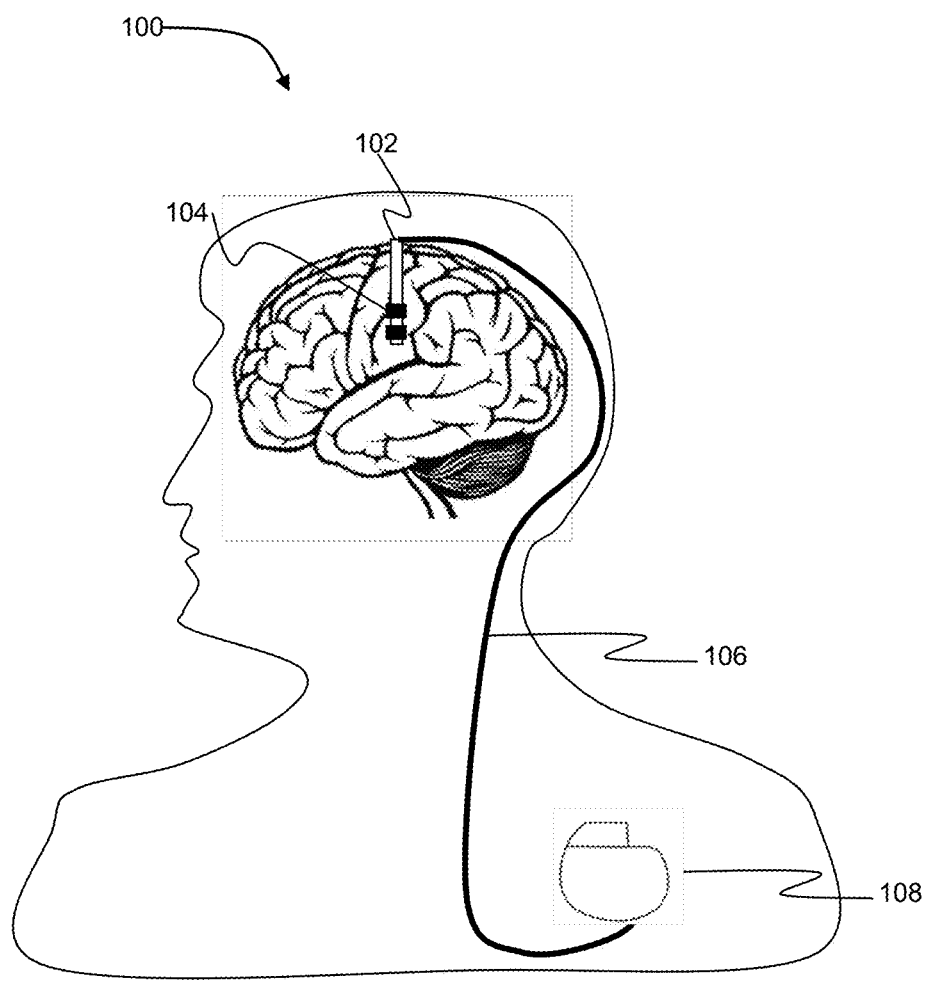
FIG. 1 is a side view depicting a deep brain stimulation system implanted into the body of a patient, according to an embodiment.

While embodiments are amenable to various modifications and alternative forms, specifics thereof have been shown by way of example in the drawings and will be described in detail. It should be understood, however, that the intention is not to be limiting with respect to the particular embodiments described. On the contrary, the intention is to cover all modifications, equivalents, and alternatives falling within the spirit and scope of the appended claims.

DETAILED DESCRIPTION

FIG. 1 depicts an exemplary DBS system 100 including a lead 102 comprising one or more electrodes 104 implanted within the thalamus of the brain of a patient. Lead 102 is in electrical connection via an optional extension 106 to a pulse generator 108. In embodiments, pulse generator 108 can be implanted or external, and DBS lead 102 can be targeted to any brain region.

Figure 2:
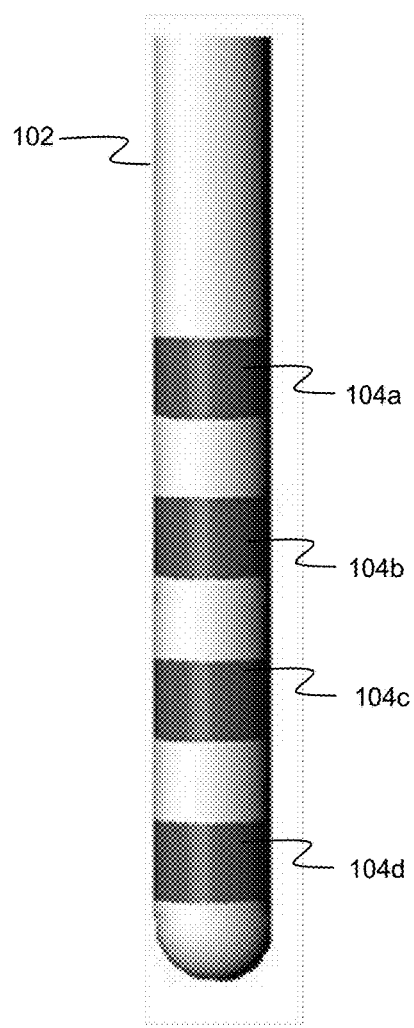
FIG. 2 is a perspective view of a deep brain stimulation lead with four electrodes, according to an embodiment.
Figure 3:
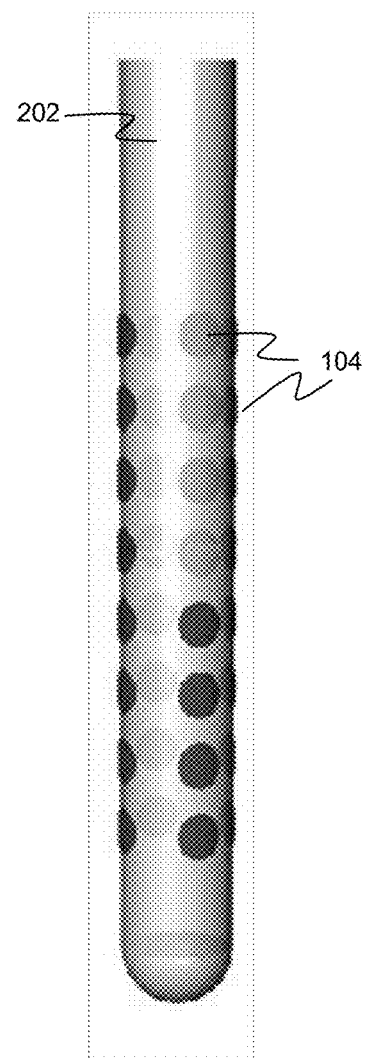
FIG. 3 is a perspective view of a deep brain stimulation lead with an array of electrodes, according to an embodiment.

FIG. 2 depicts a detailed view of lead 102 with four circumpolar electrodes 104a-d. FIG. 3 depicts a DBS array (DBSA) lead 202 with a greater number of electrodes 104 spaced radially and transversely along lead 202. Leads 102 and 202 can include an insulating layer surrounding conductors (not shown) providing electrical connection from electrodes 104 to pulse generator 108. Leads 102 and 202 are examples of suitable leads, and other configurations, arrangements and types of leads can be used in various embodiments discussed herein.

Figure 4:
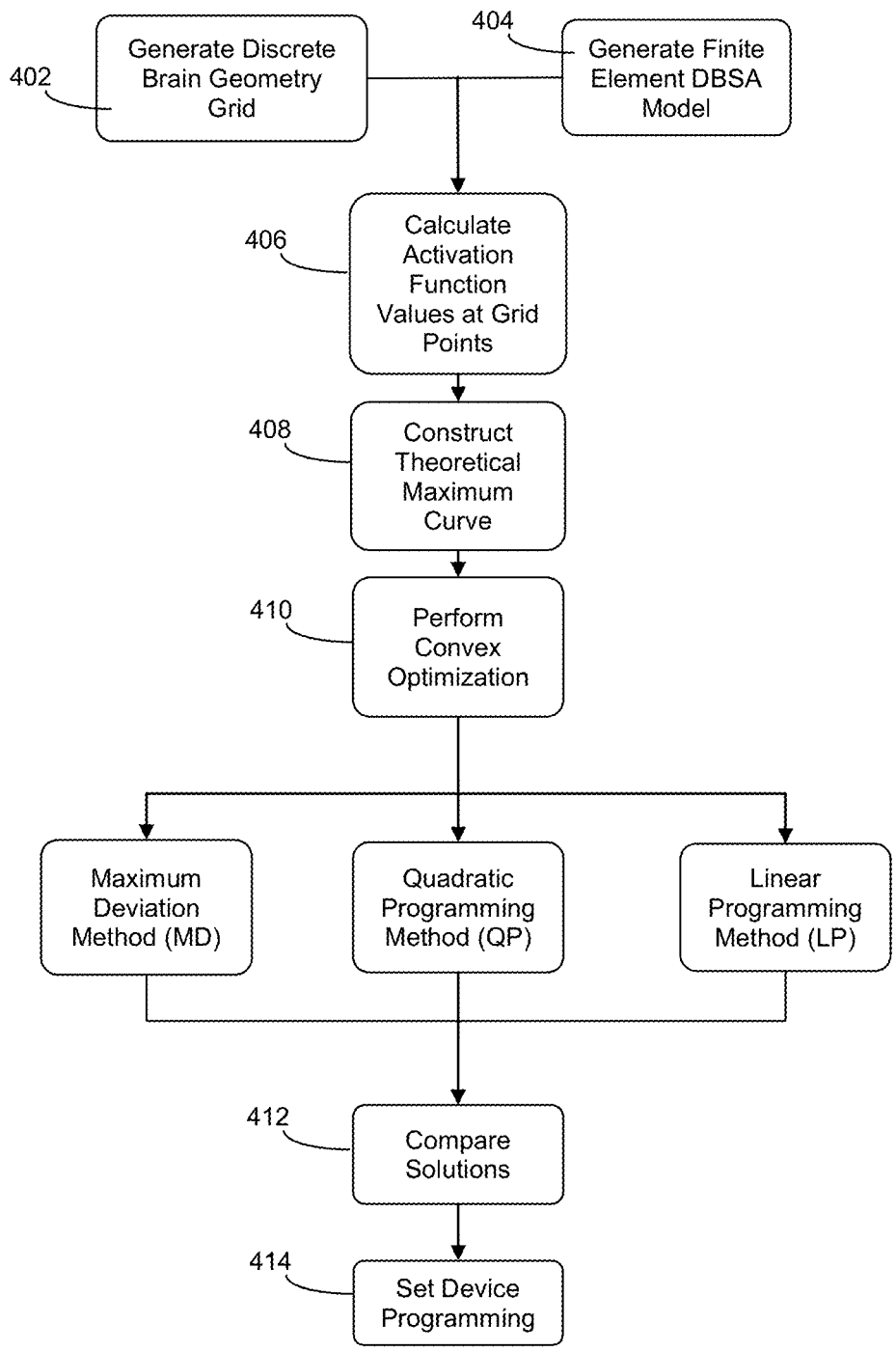
FIG. 4 is a flowchart depicting a method of generating stimulation settings for a deep brain stimulation array, according to an embodiment.

Embodiments of the present disclosure are directed to determining and providing therapies by electrical stimulation of one or more electrodes 104 by pulse generator 108. FIG. 4 is a flowchart depicting an overview of a method by which pulse generator 108 can be programmed with settings for each electrode that provide maximum stimulation to one or more target regions while minimizing stimulation of side effect regions. Though this will be discussed in more detail below, including in the context of examples of related systems, hardware and other features, the overview related to FIG. 4 can be helpful for appreciating various features individually and in combination.

At 402, brain geometry data unique to a specific patient (for example MRI data) can be combined with brain atlas data to generate a discrete brain geometry grid. Data regarding the configuration of the electrodes 104 on the implanted lead 102 or 202 can be used to generate a finite element model of the electrode configuration at 404. At 406, an activation function (AF) value at each of the grid points can be calculated and used to construct a theoretical Max Curve at 408. The Max Curve represents the greatest likelihood for cellular depolarization that can be transferred to any grid point given a fixed amount of current generated by pulse generator 108. The Max Curve can be used as criteria for convex optimization via one or more optimization methods (such as convex optimization in one embodiment) at 410 to determine how much energy to output to each electrode. The solutions can be compared at 412, and device programming can be set and/or carried out at 414. In other embodiments, more or fewer activities can be carried out, such that additional activities not depicted in FIG. 4 can be included, or activities that are depicted can be omitted.

Figure 5:
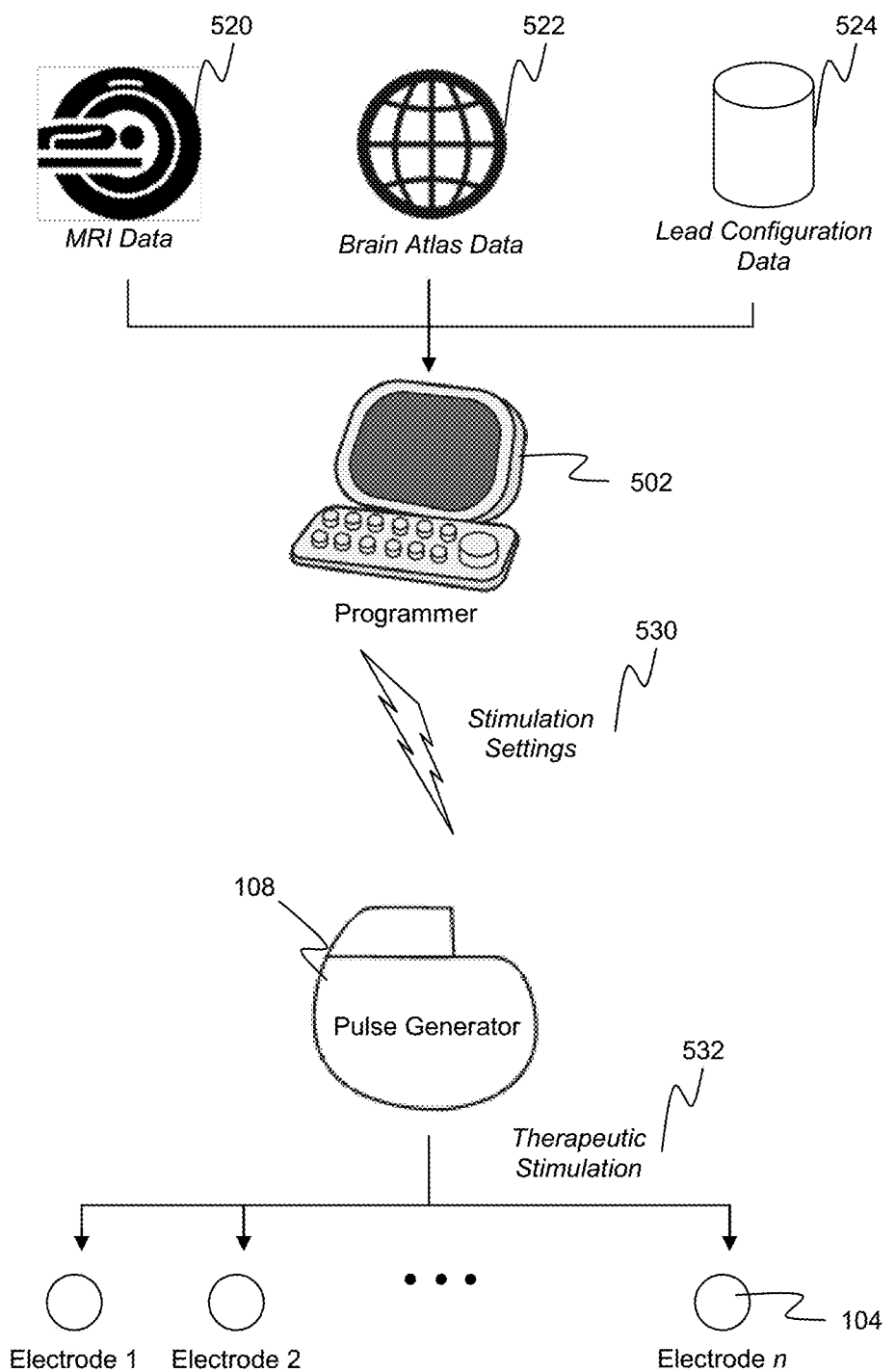
FIG. 5 is a block diagram depicting a deep brain stimulation system and a programmer, according to an embodiment.

Embodiments can include systems of hardware and software adapted to carrying out the activities depicted in FIG. 4 above. FIG. 5 depicts an example system in which MRI data 520, brain atlas data 522 and lead configuration data 524 are used by a programmer device 502 and pulse generator 108 in order to provide optimally programmed therapeutic stimulation 532 to electrodes 104. The data sources 520, 522, and 524 can be used by programmer device 502 to determine stimulation settings 530 that are customized to the patient. In various embodiments, all three data sources 520, 522, 524 can be used, or fewer than all three can be used. Programmer device 502 can be electrically and/or communicatively coupled to or otherwise receive data from some or all of data sources 520, 522, 524. Pulse generator 108 directs therapeutic stimulation currents 532 according to the stimulation settings 530, which can be determined by programmer device 502 based at least in part on the data from data sources 520, 522, 524. In still other embodiments, data from different or additional data sources also or instead can be communicated to programmer device 502 for consideration in determining stimulation settings 530.

Figure 6A:
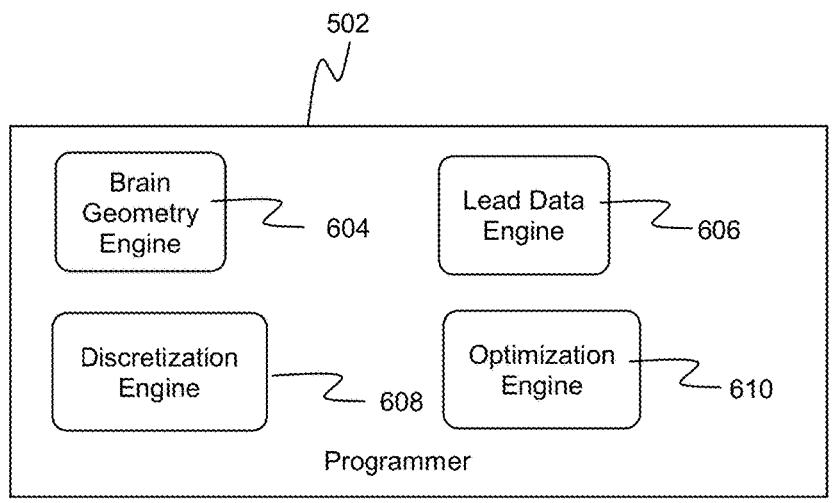
FIG. 6A is a block diagram depicting a programmer, according to an embodiment.

Pulse generator 108 is in wired or wireless communication with programmer device 502. Programmer device 502 can be a handheld device, laptop or desktop computer, server, tablet, cellular or smart phone or other computing device capable of communication with pulse generator 108. Programmer device 502 can present a user interface adapted to allow a user, such as a clinician, patient, or researcher, to review, monitor, and update device data and settings. As can be seen in FIG. 6A, programmer device 502 can comprise a brain geometry engine 604, lead data engine 606, discretization engine 608, and optimization engine 610. Engines 604, 606, 608, 610 can be software, firmware, hardware or combinations thereof in embodiments and can comprise or be controlled, executed and/or coupled by a processor, such as a microprocessor, or other computing device. In still other embodiments, engines 604, 606, 608, 610 can be different functions, routines, algorithms, functional units, of a processor or other device. Examples of the tasks, activities and other characteristics of engines 604, 606, 608, 610 are discussed below. Other components of programmer 502, including hardware and software components, can be included but are not specifically depicted in FIG. 6A.

Figure 6B:
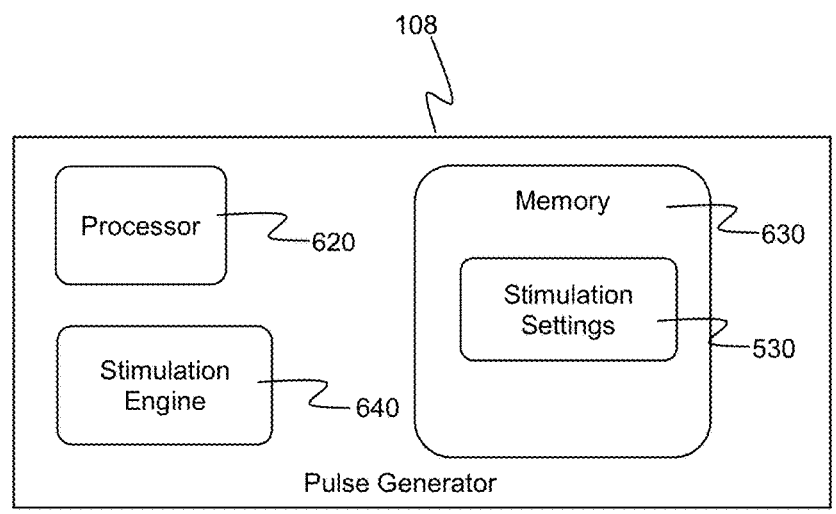
FIG. 6B is a block diagram depicting a pulse generator, according to an embodiment.

As can be seen in FIG. 6B, pulse generator 108 can comprise a processor 620 and a memory 630. Memory 630 can include storage for stimulation settings 530 for each of electrodes 104 present on lead 102 or 202. Stimulation settings 530 can be, for example, an array, hash table, dictionary, database or other data structure keyed to each electrode 104. The value at each key can be the amount of current (for example, in milliamps) to be directed to each electrode 104 during a therapy pulse. Stimulation settings 530 can also include other data items such as pulse time, pulse interval, or current or voltage timing voltages for ramped or shaped pulses. Pulse generator 108 can also have a communication engine, capable of wired or wireless communication with programmer device 502. Pulse generator 108 can also have one or more sensing engines capable of interpreting data sensed by electrodes 104 or via sensors within pulse generator 108 itself. Pulse generator 108 can have a stimulation engine 640 capable of independent current-controlled stimulation through each electrode 104 provided. In embodiments, pulse generator 108 can house any of brain geometry engine 604, lead data engine 606, discretization engine 608, and optimization engine 610 instead of or in addition to the engines in programmer 502.

In operation, pulse generator 108 can provide therapy to brain or other tissue by directing pulses of electrical current to each electrode 104 based on the values stored in stimulation settings 530. In order to determine optimum stimulation settings that maximize therapeutic value while minimizing side effects, patient and lead specific data can be combined by programmer 502 in order to determine optimum stimulation settings 530.

Returning now to FIG. 6A, the various engines of programmer 502 will be described in more detail. Each of the engines can be adapted to perform one or more of the activities of the method discussed regarding FIG. 4, for example.

Brain geometry engine 604 is adapted to receive brain geometry data and generate a three-dimensional (3D) rectangular grid of multiple layers corresponding to the tissue that is the target of stimulation (i.e., generate a discrete brain grid at 402 of FIG. 4). Brain geometry data can include MRI data 520 which can be produced via magnetic resonance imaging (MRI) of the patient. MRI data 520 can comprise susceptibility weighted imaging (SWI) in one embodiment.

Figure 7:
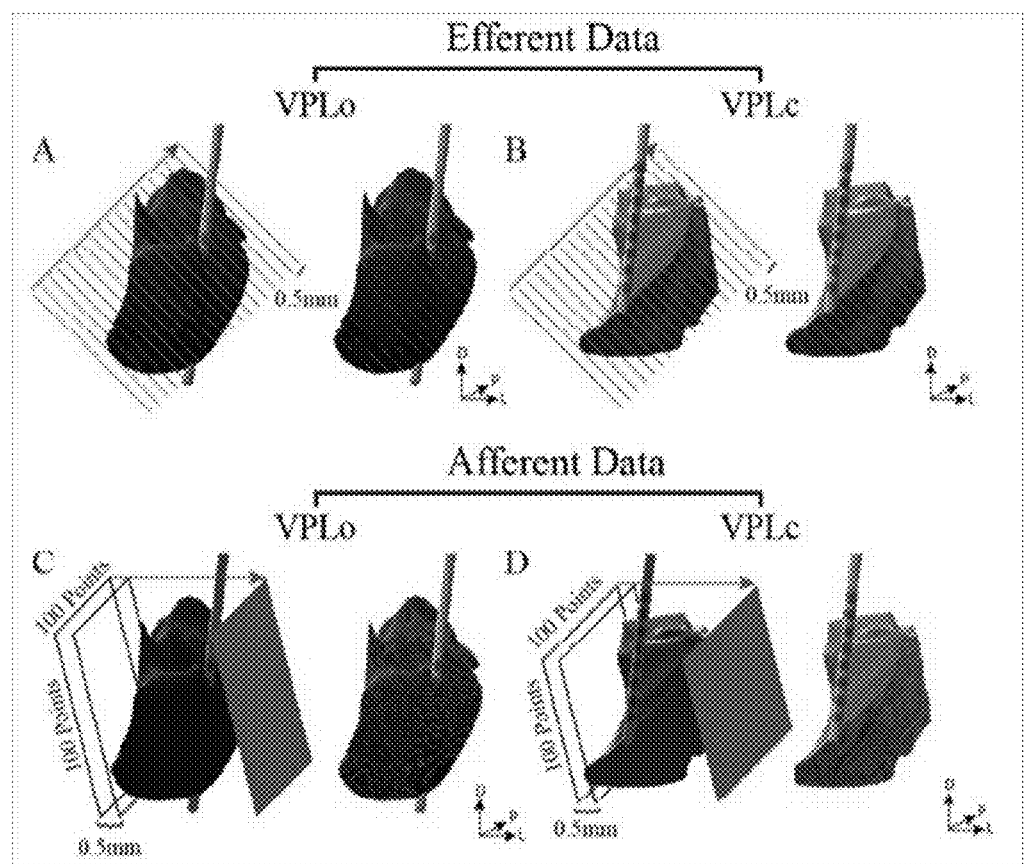
FIG. 7 is a simulated view of a discretized brain volume according to an embodiment.

In embodiments, brain geometry engine 604 then can obtain coronal images from the MM data and use those images to contour the target tissue. Returning to the above example, brain geometry engine 604 can align the acquired SWI data to the anterior commissure (AC)-posterior commissure (PC) plane and slice it to produce serial coronal sections. These coronal sections, or images, can be analyzed to identify those that span the target tissue and matched to places from a tissue atlas (for example, a brain atlas 522) in order to extract the contours of the target tissue. Brain geometry engine 604 can then map the contours onto a 3D rectangular grid of axon nodal locations (e.g., in both the afferent and efferent directions from thalamus) as can be seen in FIG. 7. This is just one example, however, and those skilled in the art will appreciate that other MRI data and acquisition sequences, as well as other mapping techniques, can be used in other embodiments.

Lead data engine 606 is adapted to generate and store a finite element model (FEM) of the voltage distribution resulting from electrical stimulation through each of electrodes 104 on lead 102 or 202 (i.e., generate a finite element DBSA model at 404 of FIG. 4). The electrode surfaces can be designated as boundary current sources, and the walls of the bulk tissue cylinder can be set to ground. The voltage distributions resulting from electrical stimulation through the electrodes can be calculated, such as via the finite element method by solving Poisson's equation. Stimulation then can be performed for each electrode 104. In one embodiment, the stimulation comprises monopolar cathodic or anodic stimulation (e.g., at ±1 mA), with each of the electrodes acting as the cathode and then the anode (or vice-versa). Programmer device 502 can calculate the finite element model, or the calculated data can be provided to programmer device 502 by a user. Programmer device 502 can optionally store finite element models for multiple forms of leads 102 or 202.

Discretization engine 608 is configured to determine the maximum AF value possible at each point in the grid produced by brain geometry engine 604, and to construct the theoretical maximum curve also known as the Max Curve (such as at 406 and 408 in FIG. 4). In one embodiment, discretization engine 608 first calculates the activation function values at each grid point along the fiber direction. This can be done, for example, using the following formula in one embodiment:

$$\frac{\partial^2 V}{\partial x^2} = \frac{V(x + \Delta x) - 2V(x) + V(x - \Delta x)}{\Delta x^2}$$

in which x is a position along the direction of the fibers, V is the voltage value as a function of position, and $\Delta x$ is the internodal distance. In other words, the AF is the second spatial derivative of the voltage within the target tissue at each grid point. This formulation for the AF is just one example, however, and those skilled in the art will appreciate that choice of other formulations can be made in other embodiments. Notably, other functional derivatives can be used in place of AF to represent depolarization at the grid points. This includes first spatial derivatives as well as second spatial derivatives that incorporate multiple fiber directions. Points that overlap spatially with the DBSA can also be discarded.

The AF values for the remaining n points can be stored in a matrix. In one embodiment, the matrix can comprise an m×n matrix C, where m is the total number electrodes, the $i^{th}$ row contains the AF values resulting from stimulation through the $i^{th}$ electrode alone, delivering −1 mA monopolar cathodic current. An example of matrix C is:

$$C = \begin{pmatrix} \nabla^2_{1,1} & \cdots & \nabla^2_{1,n} \\ \vdots & \ddots & \vdots \\ \nabla^2_{m,1} & \cdots & \nabla^2_{m,n} \end{pmatrix}$$

Poisson's equation in electrostatics dictates that voltage distribution is proportional to the current, $\nabla \cdot \sigma \nabla V = -I$, where $\sigma$ is the specific electrical conductivity of the tissue and I is the current. From this, it is possible to derive that the current changes with the second derivative of the voltage. Therefore, it can be shown that the AF values resulting from multiple voltage sources can be linearly superimposed. To find the maximum possible AF at a given grid point from any possible electrode configuration (subject to, for example, a 1 mA power constraint), the following thought experiment can be considered: Suppose there are n different categories of items that can be manufactured, each with the same cost but different profit margins. For a given manufacturing budget, the highest profit achievable occurs when the entire budget goes into manufacturing the most profitable item. Likewise, it can be readily shown that the highest possible AF value achievable at each grid point is obtained when stimulating through a single electrode using the maximum allowable current (e.g., 1 mA). Therefore the maximum value in each column (j) of the C matrix is the theoretical maximum AF value possible for grid point j. The maximum AF values can be sorted in ascending order and arranged into a Max Curve. Each grid point represents the center of a membrane compartment and has potential to be the point of initiation of an action potential. Positive AF values are responsible for directly depolarizing the cell membrane and are considered here as potential initiation sites for action potential generation. Negative AF values represent direct hyperpolarization of the cell membrane and thus can limit the likelihood of generating action potentials.

Optimization engine 610 can use the Max Curve values calculated by discretization engine 608 as a goal to reach when determining optimum stimulation settings 530 (such as at 410 of FIG. 4). The AF values due to a given electrode configuration can be denoted $AF_j = C_j^T I$, where I is the n×1 vector of current through each electrode, n is the number of electrodes, and $AF_j$ and $C_j$ are the AF value and column of C corresponding to grid point j. Together the AF values resulting from stimulation at each grid point can form another curve called the Actual Curve. At each grid point j, the difference between the maximum AF value and the actual AF value from stimulation with I is given by the following: $AF_{j,max} - AF_j = C_{j,max} - C_j^T I$.

Optimization engine 608 can then attempt to minimize this discrepancy by one of a variety of optimization methods using well-posed problems, which have unique and global minimums. These optimization methods can include, but are not limited to, linear programming, quadratic programming, and maximum deviation. An example of each method is given below.

In one embodiment, linear programming (LP) can be used to minimize the difference between the Max Curve and the Actual Curve by solving:
minimize: $\Sigma(C_{j,max} - C_j^T I)$
subject to: $\Sigma I_k = 1$ and $I_k \geq 0$, for all k In one embodiment, quadratic programming (QP) can be used to minimize the square of the difference between the Max Curve and the Actual Curve by solving:
minimize: $\Sigma(C_{j,max} - C_j^T I)^2$
subject to: $\Sigma I_k = 1$ and $I_k \geq 0$, for all k In one embodiment, the maximum deviation (MD) between the Max Curve and the Actual Curve can be used to solve the following convex optimization problem:
minimize: $\max_j (C_{j,max} - C_j^T I)$
subject to: $\Sigma I_k = 1$ and $I_k \geq 0$, for all k In the embodiments above, the equations can be constrained by assuming that the sum of currents through all electrodes ($\Sigma I_k$) be equal to the maximum allowable current (e.g., 1 mA), and that the current through each electrode $I_k$ be greater than or equal to zero. It will be appreciated, however, that these constraints are arbitrarily defined and can be adjusted as necessary. In embodiments, the constraints can be defined in the context of using total current amplitudes that do not express stimulation-evoked side effects. In embodiments, the constraints can be defined based on user-specific battery power constraints, for example, by raising or lowering the total sum of the currents.

For example, in an embodiment, one or more side effect regions can be incorporated within the objective function so optimization engine 610 can generate stimulation settings 530 that maximally stimulate a region or regions of interest while minimally stimulating one or more side effect regions within the brain. This can be done by summing the side effect region(s) with the region(s) of interest. This sum has coefficients that represent the relative weightings of the region(s) of interest and the side effect region(s). Optimization engine 610 can allow for the adjustment of the weighting as desired to increase stimulation of the region(s) of interest while minimizing side effects. Thus, this weighting-based programming approach requires only adjusting a single variable, which significantly reduces the complexity of programming even below current clinical approaches. Notably, this simplification still leverages the current steering capabilities of high density DBS arrays.

In embodiments, the constraints on the current through each electrode, $I_k$, can be adjusted to support optimization of anodal as well as cathodal current by allowing $I_k$ to be less than zero. This can enable bipolar or multi-polar combinations to be included as well.

Figure 8:
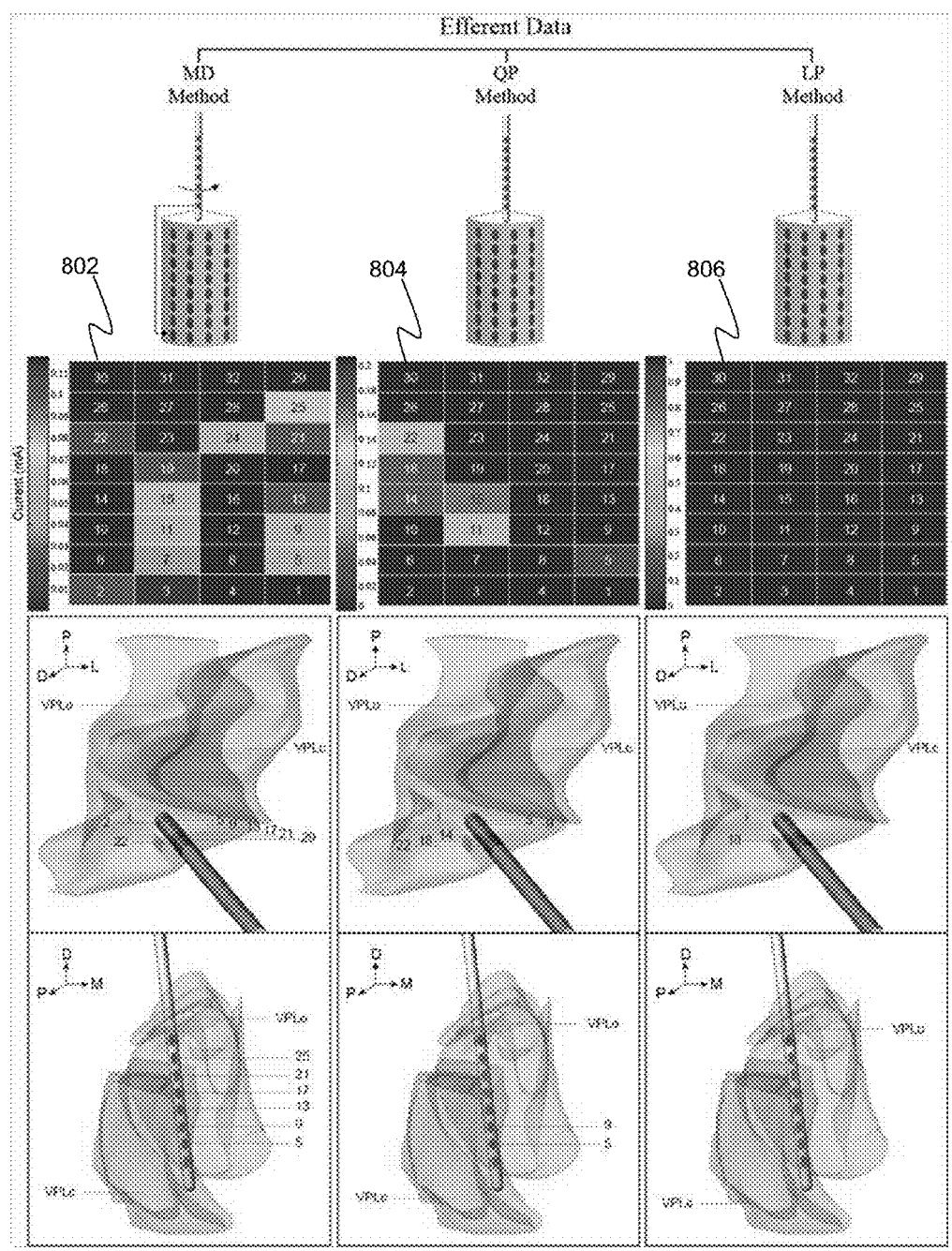
FIG. 8 is a simulated view of the results of generating stimulation settings according to embodiments.

FIG. 8 depicts example therapy configurations generated via each of the MD method 802, QP method 804, and LP method 806 for a device implanted in the thalamus of a non-human primate with a DBS array having 32 electrodes. Each potential configuration 802, 804, 806 is a group of stimulation settings 530 that can be provide to, or programmed into, pulse generator 108. In each configuration 802, 804, 806, each electrode 1-32 is assigned a color corresponding to the amount of current assigned to it for each pulse. As can be seen in FIG. 8, in this case, the MD method 802 produces the most active contacts, whereas the LP method 806 has the smallest number of contacts with all of the current being supplied to electrode 18.

If multiple solutions are generated, they can be compared to determine the actual device settings to use (such as at 412 of FIG. 4). In embodiments, optimization engine 610 can generate solutions for each optimization method and present them to the user of programmer device 502 to choose the ideal therapy configuration for the patient. In other embodiments, optimization engine 610 can select among the solutions and apply the therapy configuration directly (such as at 414 of FIG. 4). The skilled artisan will appreciate that there are many possible criteria for selecting a final solution. In some embodiments, the chosen solution might be the solution that activates the most (or the fewest) electrodes. In other embodiments, the chosen solution may be one that avoids activating certain electrodes. In still other embodiments, the chosen solution may involve averaging the current values at each electrode across the potential solutions. Yet further embodiments may use the other criteria, such as power consumption, or a combination of criteria in order to choose a solution.

Embodiments of this disclosure present several advantages over conventional methods and systems. For example, embodiments allow for automated programming of deep brain stimulation settings via tools that are simple to implement and use. The programming can be achieved quickly and efficiently and is thus amenable to deployment as part of a <1 hr clinical visit.

Embodiments also allow for full exploration of the potential capabilities of a DBS array that would be unable to be manually navigated. Embodiments provide definitive solutions to optimal stimulating electrode configurations and are software-based and not reliant on hardware sensing capabilities, or the continuous sensing of new patient data.

The disclosed embodiments are also patient-specific as opposed to relying on accumulated patient data to map out potential therapeutic targets for stimulation in a new patient. Accumulation of such patient databases is not feasible for those who do not have direct access to such data. Although stimulation targets for certain disorders (such as Parkinson's disease and Essential tremor) are well established, therapeutic "hot spots" may be different from patient to patient and cannot be generalized. Embodiments use patient-specific data (for example, MRI data) to identify the therapeutic target region, and maximize the probability of neuronal activation based on theories of cellular excitation.

Embodiments also do not rely on resource-heavy simulations. While it is possible to empirically determine the volume of tissue activated from virtual stimulation of realistic neuron models, such an approach would have to consider many different scenarios, including locations and orientations of the neurons with respect to the DBS array, as well as the electrode combinations and current distributions to use.

The values and particular formulas given above are examples and should not be read as limiting the scope of this disclosure. Those skilled in the art will recognize that the above values and formulas may be adjusted as necessary depending on the implantable technology used and the physical characteristics of the patient.

Thus, in an embodiment, a method for determining a stimulation setting for each electrode in a deep brain stimulation array having one or more electrodes comprises receiving brain geometry data; receiving lead geometry data; generating, from the brain geometry data and the lead geometry data, one or more grid points representing a target tissue to be activated; calculating a maximum activation function value for each of the one or more grid points; and performing a convex optimization method to determine a set of stimulation settings for each electrode such that an actual activation function value for each grid point is as close to the maximum activation function value for the grid point.

In embodiments, the convex optimization method can minimize the maximum deviation between the actual activation function value and the maximum activation function value for each axonal grid point.

In embodiments, the convex optimization method can minimize the sum of the square of the differences between the actual activation function value and the maximum activation function value for each grid point.

In embodiments, the convex optimization method can minimize the sum of the differences between the actual activation function value and the maximum activation function value for each axonal grid point.

Additionally, in an embodiment, the stimulation settings can be configured to avoid activation of non-target tissue such that the method further comprises identifying one or more grid points representing non-target tissue to be avoided when stimulating through the one or more electrodes; determining a set of stimulation settings for at least one of the one or more electrodes such that an actual activation function value for each of the one or more non-target tissue grid points is as close as possible to the minimum activation function value calculated for each of the one or more grid points; and including the set of stimulation settings for at least one of the one or more electrodes in the providing to the pulse generator.

In embodiments, computing devices, microprocessors and other computer or computing devices discussed herein can be any programmable device that accepts digital data as input, is configured to process the input according to instructions or algorithms, and provides results as outputs. In an embodiment, computing, processor and/or other such devices discussed herein can be, comprise, contain or be coupled to a central processing unit (CPU) configured to carry out the instructions of a computer program. Computing, processor and/or other such devices discussed herein are therefore configured to perform basic arithmetical, logical, and input/output operations.

Computing, processor and/or other devices discussed herein can include memory. Memory can comprise volatile or non-volatile memory as required by the coupled computing device or processor to not only provide space to execute the instructions or algorithms, but to provide the space to store the instructions themselves. In embodiments, volatile memory can include random access memory (RAM), dynamic random access memory (DRAM), or static random access memory (SRAM), for example. In embodiments, non-volatile memory can include read-only memory, flash memory, ferroelectric RAM, hard disk, floppy disk, magnetic tape, or optical disc storage, for example. The foregoing lists in no way limit the type of memory that can be used, as these embodiments are given only by way of example and are not intended to limit the scope of the invention.

In embodiments, the system or components thereof can comprise or include various engines, each of which is constructed, programmed, configured, or otherwise adapted, to autonomously carry out a function or set of functions. The term "engine" as used herein is defined as a real-world device, component, or arrangement of components implemented using hardware, such as by an application specific integrated circuit (ASIC) or field-programmable gate array (FPGA), for example, or as a combination of hardware and software, such as by a microprocessor system and a set of program instructions that adapt the engine to implement the particular functionality, which (while being executed) transform the microprocessor system into a special-purpose device. An engine can also be implemented as a combination of the two, with certain functions facilitated by hardware alone, and other functions facilitated by a combination of hardware and software. In certain implementations, at least a portion, and in some cases, all, of an engine can be executed on the processor(s) of one or more computing platforms that are made up of hardware (e.g., one or more processors, data storage devices such as memory or drive storage, input/output facilities such as network interface devices, video devices, keyboard, mouse or touchscreen devices, etc.) that execute an operating system, system programs, and application programs, while also implementing the engine using multitasking, multithreading, distributed (e.g., cluster, peer-peer, cloud, etc.) processing where appropriate, or other such techniques. Accordingly, each engine can be realized in a variety of physically realizable configurations, and should generally not be limited to any particular implementation exemplified herein, unless such limitations are expressly called out. In addition, an engine can itself be composed of more than one sub-engines, each of which can be regarded as an engine in its own right.

Moreover, in the embodiments described herein, each of the various engines corresponds to a defined autonomous functionality; however, it should be understood that in other contemplated embodiments, each functionality can be distributed to more than one engine. Likewise, in other contemplated embodiments, multiple defined functionalities may be implemented by a single engine that performs those multiple functions, possibly alongside other functions, or distributed differently among a set of engines than specifically illustrated in the examples herein.

Various embodiments of systems, devices and methods have been described herein. These embodiments are given only by way of example and are not intended to limit the scope of the invention. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the invention.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:

1. A method for determining a stimulation setting for each electrode in a deep brain stimulation array including one or more electrodes, the method comprising:
   using brain geometry data to generate a discrete brain geometry grid;
   identifying one or more grid points in the discrete brain geometry grid, the one or more grid points representing a target tissue to be activated by stimulation through the one or more electrodes;
   calculating a maximum activation function value for each of the one or more grid points using an estimated voltage distribution of the stimulation of the one or more electrodes;
   constructing a maximum curve for the discrete brain geometry grid from the maximum activation function value of each of the one or more grid points;
   optimizing a set of stimulation settings for each of the one or more electrodes using one or more optimization methods such that an actual activation curve for the discrete brain geometry grid is as close as possible to the maximum curve of the discrete brain geometry grid; and
   providing, to a pulse generator capable of delivering therapy via each of the one or more electrodes, the set of stimulation settings for each electrode.

2. The method of claim 1, wherein the identifying comprises:
   receiving brain geometry data;
   receiving lead geometry data; and
   generating, from the brain geometry data and the lead geometry data, the one or more grid points representing the target tissue to be activated.

3. The method of claim 1, wherein the optimizing comprises minimizing a maximum deviation between the maximum activation function value and the actual activation function value for each of the one or more grid points.

4. The method of claim 1, wherein the optimizing comprises minimizing a difference between the maximum activation function value and the actual activation function value for each of the one or more grid points.

5. The method of claim 1, wherein the optimizing comprises minimizing a square of a difference between the maximum activation function value and the actual activation function value for each of the one or more grid points.

6. The method of claim 1, wherein the stimulation settings comprise electrical pulse amplitudes.

7. The method of claim 1, wherein the stimulation settings comprise electrical pulse widths.

8. The method of claim 1, wherein the optimizing comprises using an optimization routine.

9. The method of claim 1, further comprising optimizing, using a plurality of optimization routines, a plurality of sets of stimulation settings for each electrode.

10. The method of claim 1, wherein the stimulation settings are configured to avoid activation of non-target tissue such that the method further comprises:
    identifying one or more grid points representing non-target tissue to be avoided when stimulating through the one or more electrodes;
    optimizing a set of stimulation settings for each of the one or more electrodes such that an actual activation function value of the one or more grid points is as close as possible to the minimum activation function value calculated for each of the one or more grid points; and
    including the set of stimulation settings for at least one of the one or more electrodes in the providing to the pulse generator.

* * * * *